(12) United States Patent
Cunningham et al.

(10) Patent No.: US 8,805,706 B2
(45) Date of Patent: Aug. 12, 2014

(54) SYSTEMS AND METHODS FOR MANAGING INSURANCE ACCOUNT DOCUMENTS

(75) Inventors: Kathleen Anne Cunningham, Torrington, CT (US); James L. Pabilonia, Jr., Tolland, CT (US); Robert Vitti, South Windsor, CT (US)

(73) Assignee: Hartford Fire Insurance Company, Hartford, CT (US)

( * ) Notice: Subject to any disclaimer, the term of this patent is extended or adjusted under 35 U.S.C. 154(b) by 0 days.

(21) Appl. No.: 13/097,560

(22) Filed: Apr. 29, 2011

(65) Prior Publication Data

US 2012/0278107 A1    Nov. 1, 2012

(51) Int. Cl.
*G06Q 40/00*    (2012.01)

(52) U.S. Cl.
USPC ................................. 705/4; 705/35

(58) Field of Classification Search
USPC ..................... 705/2, 3, 4, 35, 38, 39
See application file for complete search history.

(56) References Cited

U.S. PATENT DOCUMENTS

| | | | | |
|---|---|---|---|---|
| 5,282,052 A * | 1/1994 | Johnson et al. | ............... | 358/402 |
| 6,928,487 B2 * | 8/2005 | Eggebraaten et al. | ........ | 709/246 |
| 7,194,416 B1 | 3/2007 | Provost et al. | | |
| 7,333,939 B1 | 2/2008 | Stender et al. | | |
| 7,689,444 B2 | 3/2010 | Atlee et al. | | |
| 8,095,394 B2 * | 1/2012 | Nowak et al. | ..................... | 705/4 |
| 8,108,229 B2 * | 1/2012 | Ika et al. | ........................... | 705/4 |
| 8,108,230 B2 * | 1/2012 | Ika et al. | ........................... | 705/4 |
| 2002/0026334 A1 * | 2/2002 | Igoe | .................................... | 705/4 |
| 2006/0059418 A1 * | 3/2006 | Elkady | ........................ | 715/508 |
| 2009/0171692 A1 | 7/2009 | Zilberman et al. | | |
| 2009/0210256 A1 | 8/2009 | Upadhyayula et al. | | |
| 2010/0100561 A1 * | 4/2010 | Cooper et al. | ................ | 707/769 |
| 2011/0040582 A1 | 2/2011 | Mullins | | |
| 2012/0158434 A1 * | 6/2012 | Reid | ................................ | 705/4 |

OTHER PUBLICATIONS

Anonymous "The Hartford Launches Voluntary Benefits Solutions That Removes Administration Burden for Employers, Workers" Nov. 5, 2009, Business Wire.*
Anonymous "Metlife Launches New Disability Income Term Premium Conversion Rider" Jan. 11, 2011 Business Wire.*
Davis, Phillip "Long Term Car Traps; Help Clients Who Are Interested in LTCI Avoid These Common Pitfalls" Mar. 1, 2011 Bank Investment Consultant 19.3:31.*

* cited by examiner

*Primary Examiner* — Kelly Campen
(74) *Attorney, Agent, or Firm* — Volpe and Koenig, P.C.

(57) ABSTRACT

A Personal Health Application (PHA) management system stores templates that are used to generate customized PHA documents. The PHA management system receives a request for a PHA document, where the request includes information that describes a new insurance policy or modification of a policy that an insurance consumer is requesting, that indicates the state or other area in which the insurance consumer lives, that indicates the reason that the consumer is requesting the new policy or modification, and/or other information. The PHA management system generates a PHA document based on a stored template and the information included in the request, and the generated PHA document may be provided to the insurance consumer.

20 Claims, 12 Drawing Sheets

FIG. 3

LIFE INSURANCE COMPANY _300_

CV1 = Based on employer preference and/or legal requirement, use one of: "Employee", "Applicant", "Enrollee", "Associate", or "Cast Member." _306_

V7 = Include text only if Employee has a child. _304_

[Contact] Information _302_

1. [Contact] Information
2. [[Employee]] First Name: [[Employee]] Middle Initial: [[Employee]] Last Name:
3. [[Employee]] Mailing Address (Street, Apt #):
4. [[Employee]] City: [[Employee]] State: [[Employee]] Zip Code:
5. [[Employee]] Social Security Number: [[Employee]] ID # (if any): [[Employee]] Date of Birth (mm/dd/yyyy):
6. [[Employee]] Daytime Phone: [[Employee]] Evening Phone:
7. [[Employee]] Email Address: [[Employee]] Occupation:
8. [[Employee]] Gender (check one): ☐ M ☐ F  [[Employee]] Height (ft./in.): [[Employee]] Weight (lbs.):
9. [[Spouse]] First Name: [[Spouse]] Last Name:
10. [[Spouse]] Daytime Phone: [[Spouse]] Evening Phone:
11. [[Spouse]] Email Address: [[Spouse]] Date of Birth (mm/dd/yyyy):
12. [[Spouse]] Gender (check one): ☐ M ☐ F  [[Spouse]] Height (ft./in.): [[Spouse]] Weight (lbs.):
13. [[Child]] First Name: [[Child]] Last Name:
14. [[Child]] Daytime Phone: [[Child]] Evening Phone:
15. [[Child]] Email Address: [[Child]] Date of Birth (mm/dd/yyyy):
16. [[Child]] Gender (check one): ☐ M ☐ F  [[Child]] Height (ft./in.): [[Child]] Weight (lbs.):

Group Benefits Coverage Information — 410

Employer Information Section — 412

| Field | Value |
|---|---|
| Employer Name | Associated Products |
| Policy Number(s) | 1234567 |
| Division (if applicable) | Salaried |
| Employer Mailing Address (Street, City, State, Zip Code) | 500 Any Street, Anytown, CT, 06790 |
| Benefits Contact Name | Lolita Paredo |
| Benefits Contact Email Address | benefits@associatedproducts.com |
| Benefits Contact Phone | 1-800-555-5555 |

Employee Information Section — 414

| Field | Value |
|---|---|
| Employee First Name | John |
| Middle Initial | Q |
| Last name | Doe |
| Base Annual Earnings* | 50,000 |
| Social Security Number | 12345678 |
| Employee ID Number | 111141 |
| Date of Election (mm/dd/yyyy) | |
| Date of Hire (mm/dd/yyyy) | 1/1/11 |
| Benefits Effective Date (mm/dd/yyyy) | |
| Reason for Application (Late, New Hire, Over GI, Opt Up, Family Status Change, or Earnings Increase) | New Hire |
| Family Status Change Effective Date (mm/dd/yyyy) | N/A |
| Earnings Increase Effective Date (mm/dd/yyyy) | N/A |

*Base annual earnings as described in the contract with The Insurance Company

Coverage Information Section — 416

- Enter the amount of any existing coverage in Current Coverage Amount that does not require Evidence of Insurability. Please include the current amount of Employee Basic Life coverage even if the Employee is not requesting Basic Life coverage at this time.
- Enter the amount of Additional Coverage Requested that requires Evidence of Insurability.
- Enter the Total Coverage Amount that will be in force if the additional coverage requested is approved.
- If the applicant is enrolling after his/her initial eligibility period and does not have current coverage they may be responsible for all fees incurred during the medical underwriting process.
- If underwriting is required for a Child, an Evidence of Insurability application will be sent to the Employee separately.

| | Current Coverage Amount that does not require Evidence of Insurability | + Additional Coverage Requested that requires Evidence of Insurability | = Total Coverage Amount |
|---|---|---|---|
| Life Insurance Coverage | Include Basic Life Current Coverage Amount even if not requesting this coverage type. | | |
| Employee Basic Life Class | 25,000 | 25,000 | 50,000 |
| Employee Supplemental Life Class | 25,000 | 25,000 | 50,000 |
| Spouse Basic Life | 10,000 | 5,000 | 15,000 |
| Spouse Supplemental Life | 10,000 | 15,000 | 25,000 |
| Is the Employee electing an amount greater than $15,000 for a Child? ☐ Yes ☐ No | Number of Children: | Amount Requested Per Child: $ | |
| Disability Insurance Coverage | All amounts should be dollars or percentage of Base Annual Earnings. Complete only if coverage requires Evidence of Insurability. | | |
| Short Term Disability Class | 50% | 20% | 70% |
| Long Term Disability Class | 60% | 10% | 70% |
| Critical Illness | | | |
| Employee Critical Illness | 5,000 | 20,000 | 25,000 |
| Spouse Critical Illness | 5,000 | 20,000 | 25,000 |

Notice

To the best of your knowledge, you are required to notify The Insurance Company in writing of any changes in your medical condition between the date you sign this form and the date the coverage is approved.
In order to complete the evaluation of this application, The Insurance Company may contact you, through the mail or over the telephone,
1. to clarify any information contained on this form;
2. to obtain any information missing from this form;
3. to ask additional questions of you or your physician about the information that you have provided; or
4. to request a paramedical exam.
We may also use information about you obtained from other sources, including our claim files, evidence of insurability applications you have previously submitted to us, copies of medical records which you have authorized us to review, and information obtained from MIB, Inc. Please note that any information received from MIB, Inc. is used in determining Evidence of Insurability for Critical Illness only. It will not be used in determining Evidence of Insurability for Life or Disability. Only information that is relevant to determining Evidence of Insurability for the coverage which you are currently requesting will be considered.

Authorization

I understand that The Insurance Company may disclose the information in its files to its reinsurer(s), MIB, Inc. (please note that any information received from MIB, Inc. is used in determining Evidence of Insurability for Critical Illness only, and will not be used in determining Evidence of Insurability for Life or Disability), other insurance companies, other persons and/or organizations performing business functions on behalf of The Insurance Company, or as required by law, including any mandated reporting to state agencies. I understand that I may request details about any of the information gathered about me that relates to this application and that such requested information and the identity of the source of the information shall be released to me or, in the case of medical information, to a licensed medical person of my choice.

Further, I authorize The Insurance Company to complete a Personal History Interview.

I agree that a photocopy of this authorization is valid as the original and understand that I or my authorized representative is entitled to receive a copy of this authorization upon request.

This authorization shall be valid for 24 months from the date signed below. This authorization may be revoked upon written request to THe Insurance Company, except to the extent that action has already been taken. However, I understand the revocation may be a basis for denying my insurance application and/or coverage and benefits.

Fraud

Any person who knowingly presents a false or fraudulent claim for payment of a loss or benefit or knowingly presents false information in an application for insurance is guilty of a crime and may be subject to fines and confinement in prison.

Certification

I hereby certify that I have reviewed the above questions and that all statements and answers contained herein are full, complete, and true to the best of my knowledge and belief. I also hereby certify that I have read and received a copy of The Insurance Company's Notice of Insurance Information Practices.

This application will be made a part of the Policy.

*FIG. 4D*

Applicant Information

| First and Last Name | Employee | Spouse | Gender (check one) | Height (ft./in.) | Weight (lbs.) | Date of Birth (mm/dd/yyyy) |
|---|---|---|---|---|---|---|
| Jane Doe | ☐ | ☒ | ☐ M ☒ F | | | |

Medical Information

Please answer the following questions to the best of your knowledge and belief. Check a "Yes" or "No", for each question.

| Question | Yes | No |
|---|---|---|
| Within the past 5 years, have you used any controlled substances with the exception of those prescribed by your physician, received medical advice or sought treatment for drug use or alcohol abuse, or been convicted of operating a motor vehicle while under the influence of drugs or alcohol? | ☐ Yes | ☐ No |
| Are you currently undergoing any diagnostic without a final diagnosis or resolution? | ☐ Yes | ☐ No |
| Within the past 5 years, have you been diagnosed with or treated by a member of the medical profession for Acquired Immune Deficiency Syndrome (AIDS) or AIDS Related Complex (ARC)? | ☐ Yes | ☐ No |

Please answer the following question to the best of your knowledge and belief. Within the past 5 years, have you been diagnosed with, treated for, or had any known symptoms due to any of the following conditions or treatments listed?

| Condition | Yes | No | Condition | Yes | No |
|---|---|---|---|---|---|
| Heart-Related Surgery or Heart Attack | ☐ Yes | ☐ No | Arthritis | ☐ Yes | ☐ No |
| Stroke | ☐ Yes | ☐ No | Muscular Dystrophy | ☐ Yes | ☐ No |
| Heart Disease (Do not check "Yes" for High Blood Pressure and/or Heart Murmur only) | ☐ Yes | ☐ No | Multiple Sclerosis (MS) | ☐ Yes | ☐ No |
| Blocked Arteries (including Arteriosclerosis, Atherosclerosis, Aneurysm, or Deep Vein Blood Clot) | ☐ Yes | ☐ No | Amyotrophic Lateral Sclerosis (ALS) | ☐ Yes | ☐ No |
| Chronic Obstructive Pulmonary Disorder (COPD) | ☐ Yes | ☐ No | Chronic Fatigue Syndrome | ☐ Yes | ☐ No |
| Sleep Apnea | ☐ Yes | ☐ No | Fibromyalgia | ☐ Yes | ☐ No |
| Emphysema | ☐ Yes | ☐ No | Psychotic/Personality Disorders | ☐ Yes | ☐ No |
| Diabetes | ☐ Yes | ☐ No | Bipolar Disorder | ☐ Yes | ☐ No |
| Crohn's Disease | ☐ Yes | ☐ No | Bipolar Disorder | ☐ Yes | ☐ No |
| Kidney Failure/Dialysis | ☐ Yes | ☐ No | Depression If yes, please answer the following below: | | |
| Cancer (Do not check "Yes" for Basal Cell Carcinoma only) | ☐ Yes | ☐ No | Did you experience a single episode (a single period of depressed mood)? | ☐ Yes | ☐ No |
| Immune Deficiency Disorder | ☐ Yes | ☐ No | Did you experience multiple episodes (multiple periods of depressed mood with periods in-between of no depressed mood)? | ☐ Yes | ☐ No |
| Hepatitis (Do not check "Yes" for Hepatitis A only) | ☐ Yes | ☐ No | Have you been hospitalized for depression? | ☐ Yes | ☐ No |
| Cirrhosis | ☐ Yes | ☐ No | Other Mental/Nervous/ Psychiatric Disorders (including Anxiety) | ☐ Yes | ☐ No |

If Critical Illness coverage is being requested, you are also required to answer the following questions to the best of your knowledge and belief. Please check a "Yes" or "No" box, for each question.

| Question | Yes | No |
|---|---|---|
| Have you had, or been recommended to have, any heart-related surgery or major organ transplant surgery? | ☐ Yes | ☐ No |
| Have you increased your high blood pressure medication within the last 6 months? | ☐ Yes | ☐ No |
| At any time during the past 12 months to the present, have you smoked cigarettes or cigars, or used a pipe, chewing tobacco, nicotine chewing gum or snuff? | ☐ Yes | ☐ No |

SYSTEMS AND METHODS FOR MANAGING INSURANCE ACCOUNT DOCUMENTS

BACKGROUND

An insurance consumer may obtain a number of different types of insurance from an insurance company, such as but not limited to life insurance, disability insurance, and critical illness insurance. When an insurance consumer attempts to obtain a policy from an insurance company, the insurance company may request information about the consumer, to determine whether the company should accept the risk involved in issuing the policy to the consumer. Depending upon the kind of policy and other factors, the insurance company may need medical information and/or other information for the insurance consumer. To obtain this information, the insurance company may provide the consumer with a personal health application (PHA). A PHA is a form that includes a number of questions that direct the consumer to provide the relevant information (referred to as "evidence of insurability (EOI)" information) to the insurance company.

For an insurance company with operations in many different geographic regions, determining the format and contents of PHA documents can be very complex. In the United States, the activities of insurance companies are heavily regulated by the states, and many states have regulations that define the kinds of information that insurance companies are permitted to ask for in PHA documents. Further, these regulations are often different from state to state. Accordingly, an insurance company cannot simply use one PHA across many different states, but must maintain many different versions of PHA documents. This makes updating PHA documents and ensuring accuracy among many different documents difficult and time-consuming. Further, the use of group insurance plans (whereby insurance consumers obtain policies by way of a group plan via their employer or a membership organization) adds additional complexity to determining the contents of PHA documents. For example, the relationships between employers and insurance consumers, attributes of the group plans, and other factors may all affect how PHA documents should be formatted and the types of information an insurance company may ask for in PHA documents. Thus, technologies that simplify the management of PHA documents and improve the communication of EOI information between consumers and insurance companies would be advantageous.

SUMMARY

A system for generating a PHA document may include a communication interface and at least one processor. The communication interface may be configured to receive a message from a computing device that indicates a request for a PHA document, wherein the request for the PHA document relates to a request by an insurance consumer for an insurance policy within a group insurance plan offered by an employer of the insurance consumer. The at least one processor may be configured to obtain such as: consumer data that indicates one or more attributes of the insurance consumer; employer data that that indicates one or more attributes of the employer of the insurance consumer; and jurisdiction data that identifies a jurisdiction whose legal requirements apply to the PHA document. The at least one processor may also be configured to obtain template data for generating the PHA document, wherein the template data includes: information that indicates a plurality of questions that solicit EOI information; a first conditional expression that indicates whether a first question from the plurality of questions should be included in the PHA document based on at least one of the consumer data, the employer data, and the jurisdiction data; and a second conditional expression that indicates that contents of a section of the PHA document should be determined based on at least one of the consumer data, the employer data, and the jurisdiction data. The at least one processor may also be configured to generate the PHA document based on the template data, the insurance consumer data, the employer data, and the jurisdiction data. The communication interface may further be configured to transmit the PHA document to the computing device.

A computer-implemented method for generating a PHA document may include receiving, via a communication interface, a message from a computing device that indicates a request for a PHA document related to an insurance policy. The method may further include at least one processor obtaining template data for generating the PHA document, wherein the template data includes: information that indicates a plurality of questions that solicit EOI information; a first conditional expression that indicates whether a first question from the plurality of questions should be included in the PHA document based on one or more of: consumer data that indicates one or more attributes of the insurance consumer; and jurisdiction data that identifies a jurisdiction whose legal requirements apply to the PHA document. The method may further include the at least one processor generating the PHA document based on the template data, wherein the generating the PHA document includes evaluating the first conditional expression. The method may further include transmitting, via the communication interface, the PHA document to the computing device.

A computer-readable medium having processor-executable instructions stored thereon which, when executed by at least one processor, will cause the at least one processor to perform a method for generating a PHA document. The method may include receiving, via a communication interface, a message from a computing device that indicates a request for a PHA document related to an insurance policy. The method may also include obtaining template data for generating the PHA document, wherein the template data includes: information that indicates a plurality of questions that solicit evidence of insurability (EOI) information; and one or more conditional expressions for determining content to include in the PHA document. The method may also include the at least one processor generating the PHA document based on the template data, wherein the generating the PHA document includes evaluating the one or more conditional expressions. The method may also include transmitting, via the communication interface, the PHA document to the computing device.

BRIEF DESCRIPTION OF THE DRAWINGS

A more detailed understanding may be had from the following description, given by way of example in conjunction with the accompanying drawings wherein:

FIG. 3 shows a portion of a template that may be used to generate a PHA document;

FIGS. 4A-4F show an example PHA document that may be generated using the features described herein;

DETAILED DESCRIPTION

Disclosed herein are processor-executable methods, computing systems, and related technologies for the management and communication of PHA documents and related information. A central PHA management system may manage and store templates that define the contents of PHA documents, as well as define the contents of a web interface that may be used by consumers to obtain and/or modify insurance policies. The PHA management system may receive a request for a PHA document for obtaining EOI information from an insurance consumer, and generate a customized PHA document based on a template managed by the PHA management system. The contents of the PHA document may be customized according to the consumer's group insurance plan, the state whose law applies to the PHA document, attributes of the consumer, and/or other factors. Additionally, an insurance consumer may request a new insurance policy or modification of an existing policy via the web interface. If EOI information is required from the consumer, the web interface will present questions to obtain the EOI information. The content and formatting of the questions presented to the consumer may also be based on the templates managed by the central PHA management system. Because PHA documents and the questions presented by the web interface are generated dynamically in response to specific requests based on the templates, insurance consumers receive PHA documents and EOI questions that are customized for their particular circumstances. Further, when an update to a PHA template is required, an administrative user may update the template in the central PHA management system, thereby ensuring that consumers receive the most up-to-date PHA documents and EOI questions, and also ensuring consistency across the PHA documents and web interface.

Figure 1:
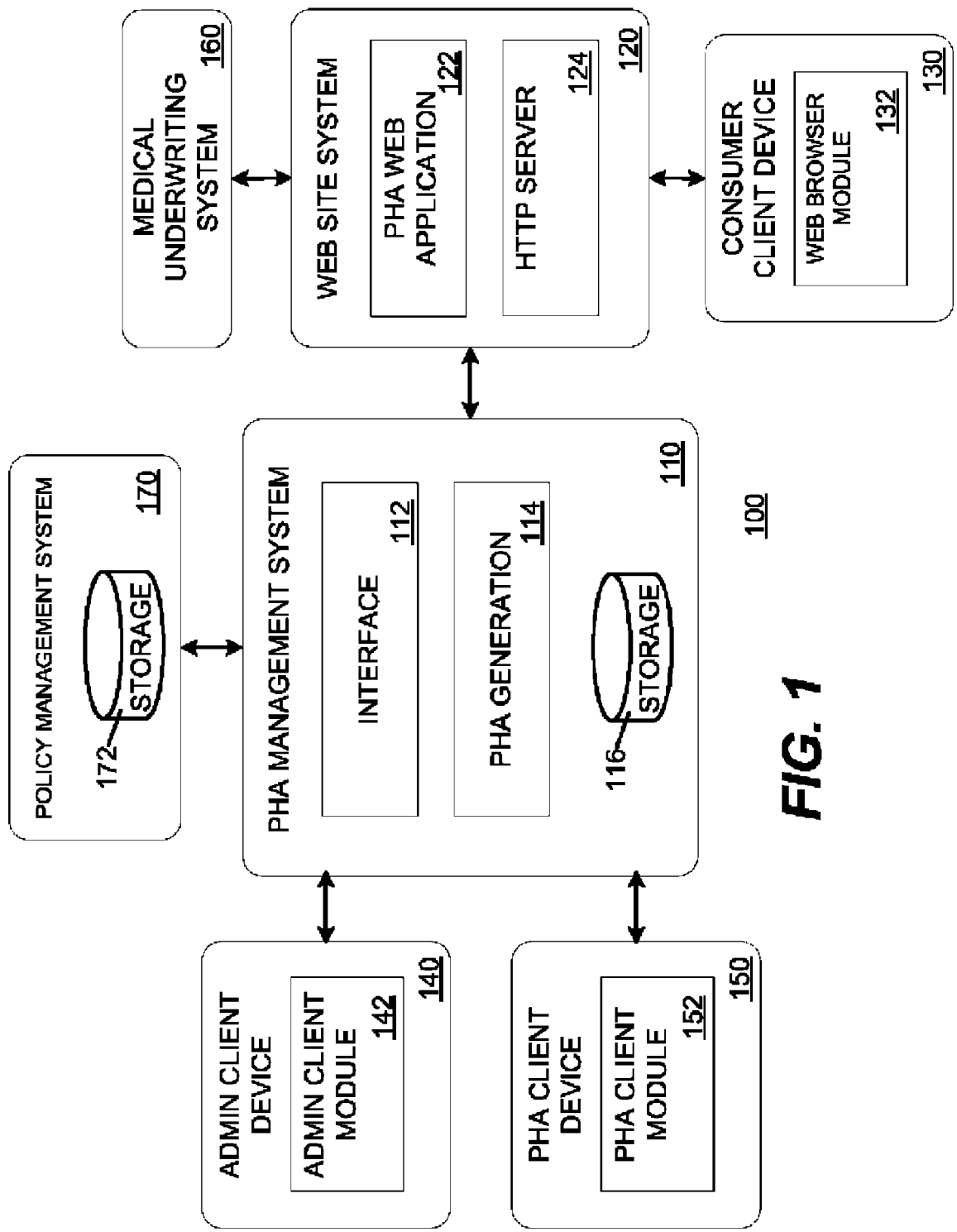
FIG. 1 shows an example architecture that may be used for the management and communication of PHA documents.

FIG. 1 shows an example architecture 100 that may be used for the management and communication of PHA documents and for requesting the issuance of an insurance policy or modification to an existing insurance policy. The example architecture 100 includes a PHA management system 110, an administrative client device 140, and a PHA client device 150. The example architecture 100 may also include a web site system 120, a medical underwriting system 160, a policy management system 170, and a consumer client device 130.

In the example architecture 100 of FIG. 1, the administrative client device 140, the PHA client device 150, the PHA management system 110, the medical underwriting system 160, the policy management system 170, and the web site system 120 are under the control of an insurance company, and the consumer client device 130 is operated by an insurance consumer. As will be described in further detail below, the PHA management system 110 generates customized PHA documents that may be provided to insurance consumers. According to this approach, an employee of the insurance company that operates the PHA client device 150 may receive a request from an insurance consumer to purchase an insurance policy or to modify an existing policy. The employee of the insurance company may then request an appropriate PHA from the PHA management system 110, and then provide the PHA to the insurance consumer. Also as will be described in further detail below, the web site system 120 provides a web site that may be accessed by an insurance consumer operating the consumer client device 130. Using this web site, the insurance consumer may provide EOI information to the insurance company, and the insurance company can indicate to the consumer whether a request for a new policy or modification has been approved.

The PHA management system 110 includes a PHA generation module 114, a PHA management database 116, and an interface module 112. The PHA generation module 114 receives input data and, using one or more PHA templates, generates customized PHA documents based on the input data. The PHA generation module 114 may also generate information that may be used by the web site system 120 for obtaining EOI data. The PHA management database 116 stores information such as the information that describes the PHA templates used by the PHA generation module 114, information that describes attributes of insurance consumers that have policies with the insurance company, and/or other information. The PHA management database 116 may be spread across one or more computer-readable media, and may be or include one or more relational databases, hierarchical databases, object-oriented databases, one or more flat files, one or more spreadsheets, and/or one or more structured files. The PHA management database 116 may be managed by one or more database management systems (not depicted), which may be based on a technology such as Microsoft SQL Server, MySQL, PostgreSQL, Oracle Relational Database Management System (RDBMS), a NoSQL database technology, and/or any other appropriate technology. Communication between the PHA management system 110 and the other elements 120, 140, 150, 170 in the example architecture 100 of FIG. 1 may be performed via the interface module 112 in the PHA management system 110. Communication between the interface module 112 and the other elements 120, 140, 150, 170 in the example architecture 100 may be performed using technologies such as Simple Object Access Protocol (SOAP), Representational State Transfer (REST), other appropriate Service Oriented Architecture (SOA) technology or web services technology, and/or other appropriate technology.

The medical underwriting system 160 performs functionality such as determining, based on one or more input parameters, whether the insurance company should issue a policy to an insurance consumer. As will be described in further detail below, the medical underwriting system 160 may communicate with the web site system 120, and may make determinations regarding whether the insurance company should issue policies in the context of the web site provided by the web site system 120.

The policy management system 170 performs functionality such as storing and processing information that describes group insurance policies and the business entities that are parties to the policies. The policy management system 170 stores this information in a policy management database 172. The policy management database 172 may be spread across one or more computer-readable media, and may be or include one or more relational databases, hierarchical databases, object-oriented databases, one or more flat files, one or more spreadsheets, and/or one or more structured files. As will be described in further detail below, the PHA management system 110 may use information from the policy management database 172 to generate PHA documents.

The administrative client device 140 is a computer or other type of data processing device or computing device, and may be operated by an employee of the insurance company to perform administrative functions for the PHA management system 110. The employee that operates the administrative client device 140 may be an employee in the legal or compliance department of the insurance company. The administrative client device 140 includes an administrative client module 142, which may be or include a web browser application, a specific-purpose client application, and/or any other appropriate type of application. The administrative client device 140 may receive input from input devices (not depicted) that are included in or connected to the administrative client device 140. These input devices may include, for example, a keyboard, a mouse, or a touch screen, and provide data that indicates the input to the administrative client module 142. The administrative client module 142 in the administrative client device 140 may communicate with the interface module 112 in the PHA management system 110. As one example, an operator of the administrative client device 140 may provide input data to the administrative client module 142 that indicates that one of the PHA templates stored in the PHA management database 116 should be updated, or that a new PHA template should be added to the PHA management database 116. The administrative client module 142 may communicate this data to the interface module 112 in the PHA management system 110, which may then update the PHA management database 116 accordingly.

The PHA client device 150 is a computer or other type of data processing device or computing device, and may be operated by an employee of the insurance company to obtain PHA documents from the PHA management system 110 to provide to insurance consumers. The operator of the PHA client device 150 may be an employee in, for example, a field services or consumer operations department in the insurance company. The PHA client device 150 includes a PHA client module 152, which may be or include a web browser application, a specific-purpose client application, and/or any other appropriate type of application. The PHA client device 150 may receive user input from input devices (not depicted) that are included in or connected to the PHA client device 150. These input devices may include, for example, a keyboard, a mouse, or a touch screen, which provide data that indicates the input to the PHA client module 152. The PHA client device 150 may also be connected to one or more printers, which may be used to print PHA documents obtained by the PHA client device. Further, the PHA client module 152 may communicate with the PHA generation module 114 in the PHA management system 110. As one example, an operator of the PHA client device 150 may receive a request from an insurance consumer for an insurance policy or a modification to an existing insurance policy. The operator of the PHA client device 150 may provide input data to the PHA client module 152 related to the request, such as an identifier of the insurance consumer, information describing the requested policy or modification, and/or other information. The PHA client module 152 may then communicate this information to the PHA generation module 114 via the interface module 112 in the in the PHA management system 110. The PHA generation module 114 may generate a PHA document that corresponds to the request, and communicate the PHA document back to the PHA client module 152 via the interface module 112. The operator of the PHA client device 150 may then provide the generated PHA document to the insurance consumer. To provide the PHA document to the insurance consumer, the PHA client device 150 may print the PHA document via a printer connected to the PHA device, and then the operator of the PHA client device may mail or fax the PHA document to the insurance consumer. Alternatively, the operator of the PHA client device may email the PHA document to the insurance consumer.

As mentioned above, the web site system 120 provides a web site that may be accessed by an insurance consumer operating the consumer client device 130. The web site system 120 includes a HyperText Transfer Protocol (HTTP) server module 124 and a PHA web application module 122. The HTTP server module 124 may implement the HTTP protocol, and may communicate HyperText Markup Language (HTML) pages and related data from the web site to/from the consumer client device 130 using HTTP. The web site system 120 may be connected to one or more private or public networks (such as the Internet), via which the web site system 120 communicates with devices such as the consumer client device 130. The web site system 120 may generate one or more web pages that request EOI information, may communicate the web pages to the consumer client device 130, and may receive responsive information from the consumer client device 130. The responsive information may include information that identifies the insurance consumer, information that describes the policy or modification that the consumer is requesting, EOI information, and/or other information. The web site system 120 may then communicate this information to the medical underwriting system 160, which may determine whether the insurance company should issue the policy. In some instances, the medical underwriting system 160 may determine that more information is required, in order to make a final decision regarding whether the insurance company should issue the policy. The web site system 120 may then communicate one or more web pages to the consumer client device 130 that indicate that the insurance company has agreed to issue the policy or that additional information is needed.

The HTTP server module 124 in the web site system 120 may be, for example, an Apache HTTP server, a Sun-ONE Web Server, a Microsoft Internet Information Services (IIS) server, and/or may be based on any other appropriate HTTP server technology. The web site system 120 may also include one or more additional components or modules (not depicted), such as one or more load balancers, firewall devices, routers, switches, and devices that handle power backup and data redundancy. The PHA web application module 122 may generate the web pages that make up the web site and that are communicated by the HTTP server module 124. The PHA web application module 122 may be implemented in and/or based on a technology such as Active Server Pages (ASP), PHP: Hypertext Preprocessor (PHP), Python/Zope, Ruby, Ruby on Rails (RoR), any server-side scripting language, and/or any other appropriate technology.

The consumer client device 130 is, for example, a cellular phone, a desktop computer, a laptop computer, a tablet computer, or any other appropriate computing device. The consumer client device 130 includes a web browser module 132, which may communicate data related to the web site to/from the HTTP server module 124 and the PHA web application module 122 in the web site system 120. The web browser module 132 may include and/or communicate with one or more sub-modules that perform functionality such as rendering HTML (including but not limited to HTML5), rendering raster and/or vector graphics, executing JavaScript, and/or rendering multimedia content. Alternatively or additionally, the web browser module 132 may implement Rich Internet Application (RIA) and/or multimedia technologies such as Adobe Flash, Microsoft Silverlight, and/or other technologies. The web browser module 132 may implement RIA and/or multimedia technologies using one or web browser plug-in modules (such as, for example, an Adobe Flash or Microsoft Silverlight plugin), and/or using one or more sub-modules within the web browser module 132 itself. The web browser module 132 may display data on one or more display devices (not depicted) that are included in or connected to the consumer client device 130, such as a liquid crystal display (LCD) display or monitor. The consumer client device 130 may receive input from the user of the consumer client device 130 from input devices (not depicted) that are included in or connected to the consumer client device 130, such as a keyboard, a mouse, or a touch screen, and provide data that indicates the input to the web browser module 132.

The example architecture 100 of FIG. 1 may also include one or more wired and/or wireless networks (not depicted), via which communications between the elements 110, 120, 130, 140, 150, 160, 170 in the example architecture 100 may take place. The networks may be private or public networks, and/or may include the Internet. In one example deployment scenario, the PHA management system 110, web site system 120, medical underwriting system 160, policy management system 170, administrative client device 140, and PHA client device 150 may communicate via one or more private networks that are under the control of the insurance company, while the consumer client device 130 may communicate with the web site system 120 via the Internet.

Each or any combination of the modules 112, 114, 122, 124, 132, 142, 152 shown in FIG. 1 may be implemented as one or more software modules, one or more specific-purpose processor elements, or as combinations thereof. Suitable software modules include, by way of example, an executable program, a function, a method call, a procedure, a routine or sub-routine, one or more processor-executable instructions, an object, or a data structure. In addition or as an alternative to the features of these modules described above with reference to FIG. 1, these modules 112, 114, 122, 124, 132, 142, 152 may perform functionality described herein with reference to FIGS. 2-7.

Figure 2:
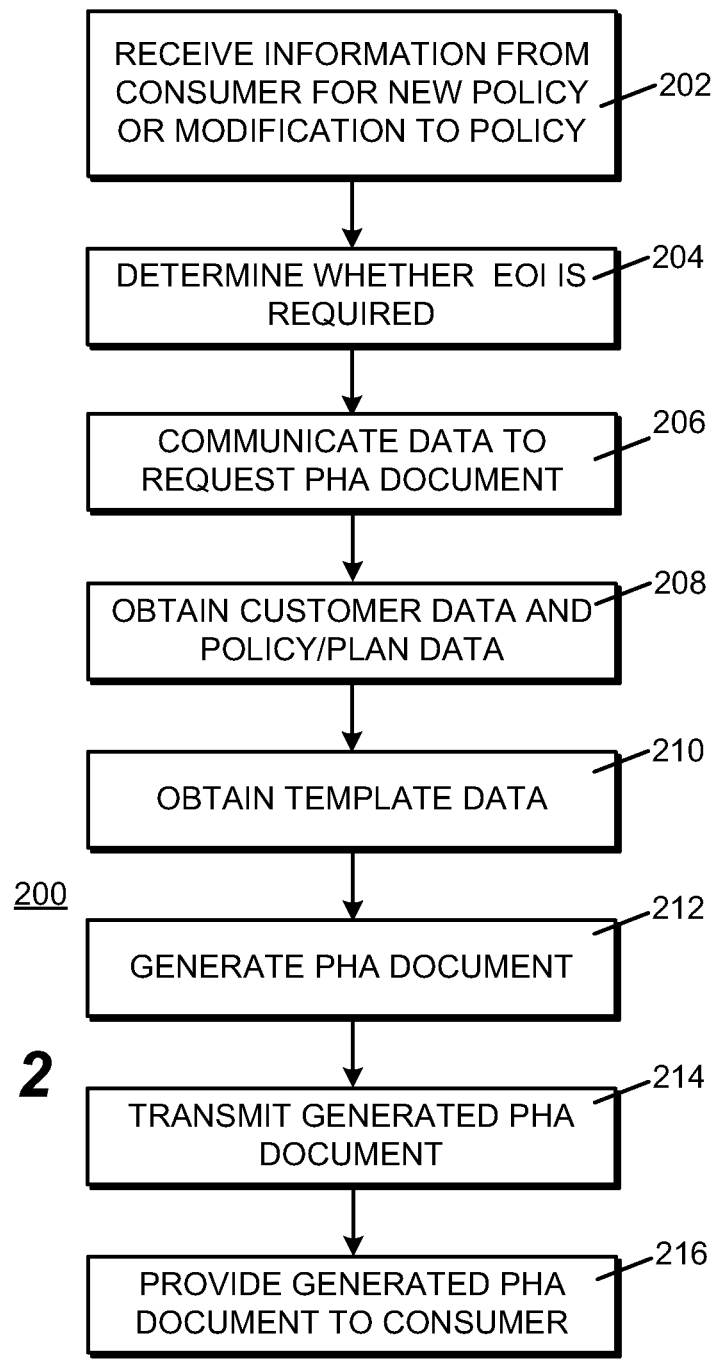
FIG. 2 shows an example method for communicating a PHA document to an insurance consumer.

FIG. 2 shows an example method 200 for communicating a PHA document to an insurance consumer using the example architecture 100 of FIG. 1. The method 200 of FIG. 2 begins with the insurance company receiving information from an insurance consumer that indicates that an insurance consumer is requesting a new policy or a modification to an existing policy (step 202). The policy at issue may be a policy for basic life insurance, supplemental life insurance, disability insurance, critical illness insurance, and/or any other type of insurance. The consumer may request the new policy during an open enrollment period for a group policy, because they were recently hired by an employer and would like to obtain a policy as part of a group policy via the employer, or because they recently joined a membership organization an would like to obtain a policy as part of a group policy via the membership organization. Alternatively, the consumer may request the policy or a modification of a policy because they have experienced a status change event such as a marriage, divorce, loss of a previously-held insurance policy, birth or adoption of a child, increase in income, or other event. Or, the consumer may request a modification to a policy because they wish to obtain a higher coverage amount on an existing policy. This information may be communicated to the insurance company in any number of ways, such as via telephone conversation, fax, email, mail, or any other appropriate mechanism. In an instance where this information is provided via telephone, mail, or fax, the operated of the PHA client device 150 may provide the information to the PHA client module 152 by inputting the information via the PHA client device 150. Alternatively, in an instance where this information is provided in an electronic format (e.g., via email or other mechanism), the PHA client module 152 may receive the information directly in an electronic format.

After receiving this information, the PHA client module 150 determines whether, in order to decide whether to issue the policy or modification, the insurance company will require EOI information (step 204). This determination may be based on attributes of the insurance consumer, attributes of a group plan offered by the consumer's employer or a membership organization of which the insurance consumer is a member, and/or other information. For example, according to a group plan by which the insurance consumer has life insurance, a coverage amount threshold may exist, above which EOI is needed and below which EOI is not needed. In an instance where the insurance consumer requests an amount above this threshold, the PHA client module 150 would make a determination that EOI is needed.

The PHA client module 150 then transmits data to the PHA management system 110 that indicates a request for a PHA document (step 206). This may include the PHA client module 152 transmitting one or more messages and/or other information to the PHA generation module 110 in the PHA management system via the interface module 112. The request may include an identifier of the insurance consumer, information that indicates the reason that the consumer is requesting the new policy or modification (e.g., a status change or they are newly hired), and/or other information.

After receiving the request for the PHA document, the PHA generation module 114 obtains input data that may be used for generating a PHA document (step 208). The input data may include data that describes attributes of the consumer, data related to a group plan offered by the consumer's employer or membership organization and/or data related to the consumer's employer or membership organization, and/or other information. To data related to the consumer, the PHA generation module 114 may read in data from and/or perform one or more searches in or queries to the PHA management database 116. The searches or queries may be based on the identifier of the insurance consumer, and/or other information related to the insurance consumer. The consumer data may include one or more of: address information for the consumer (including the state in which the consumer resides); the consumer's name; a phone number for the consumer; gender of the consumer; information that indicates whether the consumer has a spouse; information related to a spouse of the consumer, such as name, address, and gender; information that indicates whether the consumer has children; information related to children of the consumer, such as their name(s); current insurance policy information for the consumer, the consumer's spouse, and/or the consumer's children. The PHA generation module 114 may also obtain plan-related data from the policy management database 172 in the policy management system 170. The plan-related data may include data that describes the insurance consumer's employer or membership organization, a group insurance plan available through the employer or membership organization, and/or other information specific to the employer or membership organization that indicates how PHA documents for the group plan should be generated. Alternatively or additionally, the input data may include an identifier of one or more legal jurisdictions (e.g., states, territories, municipalities, and/or other governmental entities) whose legal requirements are relevant to determining the contents of the PHA.

The PHA generation module 114 then obtains data that describes a template that may be used in conjunction with the input data to generate the PHA document (step 210). This may include reading data from the PHA management database 116 that describes a template. Alternatively or additionally, this may include performing a lookup and/or issuing one or more queries to the PHA management database 116 to obtain template data. As one example, the PHA generation module 114 may perform a lookup in the PHA management database 116 based on the state in which the insurance consumer resides, to obtain a template that corresponds to the insurance consumer's state. Alternatively, the PHA generation module 114 may perform a lookup in the PHA management database 116 based on the employer or membership organization of the insurance consumer, to obtain a template that corresponds to a group plan associated with the employer or membership organization.

A template document used by the PHA generation module 114 may include, among other information, a list of questions that might be included in a finalized PHA document that is generated based on the template. The list may be exhaustive (i.e., may include the universe of all possible questions that may be included in the finalized PHA document), and the template document may include information that describes whether particular questions or groups of questions should be included in the finalized PHA document. This information may include one or more conditional expressions that indicate whether particular questions or groups of questions should be included in the finalized PHA document based on parameters such as attributes of the insurance consumer, attributes related to a group insurance plan to which the PHA document is related, attributes of the policy or modification that the insurance consumer has requested, the state or other jurisdiction whose legal requirements are applicable to the PHA document, and/or other factors. For example, a conditional expression may indicate that questions related to children of the insurance consumer should be included only if the insurance consumer has children, and/or if the policy requested by the insurance consumer relates to children of the insurance consumer. Similarly, a conditional expression may indicate that questions related to a spouse of the insurance consumer should be included only if the insurance consumer has a spouse, and/or if the policy requested by the insurance consumer related to the spouse of the insurance consumer. As a further example, a template may include a first group of questions that apply to circumstances only where an insurance consumer is interested in obtaining disability insurance, and a second group of questions that apply only to circumstances where an insurance consumer is requesting a critical illness policy; in such an instance, the template may also include a conditional expression that indicates that the first group of questions should be included when the insurance consumer is interested in obtaining disability insurance, and a conditional expression that indicates that the second group of questions should be included when the insurance consumer is interested in obtaining disability insurance. As an another example, a template document may include a question related to an insurance consumer's Human Immunodeficiency Virus (HIV) status; however, according to the law of some states, a PHA document may not include questions related to a consumer's HIV status, and so the template document may also include a conditional expression that indicates that, where the law of one of these states is applicable, the finalized PHA document should not include this question.

Further, a template document used by the PHA generation module 114 may include one or more conditional expressions that indicate that concepts identified in the template document should be described using particular words or phrases in the finalized PHD document. These variable language conditional expressions may be based on parameters such as attributes of the insurance consumer, attributes related to a group insurance plan to which the PHA document is related, attributes of the policy or modification that the insurance consumer has requested, the state or other jurisdiction whose legal requirements are applicable to the PHA document, and/or other factors. As an example, a template document may include a variable language conditional expression that indicates that, for every occurrence of the concept of "Employee," a word such as "Associate," "Cast Member," or "Worker" should be used, and that the word that should be used is specific to an employer that has a group plan to which the PHA document is related. According to this example, a first employer may prefer "Worker," while a second employer may prefer "Associate." Accordingly, a PHA document generated for a policy according to the first employer's plan may include text such as "Worker Name" and "Worker Address," while the corresponding text in a PHA document generated for a policy according to the second employer's plan may be "Associate Name" and "Associate Address." As an additional example, a template document may include a variable language conditional expression that indicates that jurisdiction-specific fraud warning language should be used, based on the jurisdiction where the insurance consumer resides. This variable language conditional expression may indicate that, for residents of the state of Florida, the following text should be used: "Any person who knowingly and with intent to injure, defraud, or deceive any insurer files a statement of claim or an application containing any false, incomplete, or misleading information is guilty of a felony of the third degree." The variable language conditional expression may also indicate that different text should be used for residents of California (e.g., "For your protection, California law requires the following to appear on this form: Any person who knowingly presents false or fraudulent claim for the payment of a loss is guilty of a crime and may be subject to fines and confinement in state prison."), as well as for other states.

Templates used by the PHA generation module 114 to generate PHA documents may be defined according to a number of different formats. For example, a template may be defined according to an Extensible Stylesheet Language Transformations (XSLT) format, a format defined according to a template technology such as MVFLEX Expression Language (MVEL), StringTemplate, Freemarker, Velocity, or other template technology, a specific-purpose template format, and/or any other appropriate format.

After obtaining data that describes a template that may be used to generate the PHA document, the PHA generation module 114 generates a PHA document (step 212). Generating the PHA document may include evaluating conditional expressions such as those described above based on the template data, the obtained consumer data, the obtained policy/plan data, and/or the information included in the request, and determining the text to include (or not include) in the PHA document based on the results of the conditional expressions. Further, generating the PHA document may include pre-filling portions of the PHA document with information related to the insurance consumer on whose behalf the PHA was requested and/or related to the employer or membership organization of the insurance consumer. The generated PHA document may be formatted according to a format such as a Microsoft Word format, Adobe Portable Document Format (PDF), Open Document Format for Office Applications (ODF) format, and/or any other appropriate format.

After generating the PHA document, the PHA generation module 114 transmits the generated PHA document to the PHA client module 152 via the interface module 112 (step 214). Then, the generated PHA document is provided to the insurance consumer on whose behalf the PHA document was requested (step 216). Providing the PHA document to the consumer may include, for example, the PHA client module 152 directly transmitting the PHA document to the consumer as an electronic message, such as an email message that includes the PHA document as an attachment. Alternatively, the user of the PHA client device 150 may provide the PHA document to the insurance consumer by emailing the PHA document to the insurance consumer. As another alternative, the user of the PHA client device 150 may print the PHA document using a printer that is connected to the PHA client device 150, and then mail or fax the PHA document to the insurance consumer.

Although not shown in FIG. 2, after the insurance consumer receives the PHA document, the insurance consumer may write the required EOI information onto the PHA document, and then mail, fax, or email the completed PHA document back to the insurance company. Alternatively, in an instance where the insurance consumer receives the PHA document in an electronic format, the insurance consumer may fill in the electronic document using a computing device, add an electronic signature to the document, and then transmit the e-signed PHA document back to the insurance company. The insurance company may then determine, using the medical underwriting system 160, whether to issue the insurance policy or modification to the insurance consumer. The insurance company may then notify the consumer of the insurance company's decision via mail, fax, email, or any other appropriate mechanism.

FIG. 3 shows a portion of a template document 300 that may be used by the PHA generation module 114 to generate a PHA document as described above with reference to the method 200 of FIG. 2. As shown in FIG. 3, the template document 300 includes a Contact Information table 302 that includes sixteen rows. Throughout the Contact Information table 302 are sets of brackets (i.e., "[" and "]" characters) that enclose phrases of text. Within each set of brackets is a label that begins with "V" (e.g., "V1," "V2," and so on) or "CV" (e.g., "CV1," "CV2," and so on). Each of the "V" labels corresponds to one or more conditional expressions that determine whether the text enclosed within the corresponding bracket should appear in the PHA document that is generated based on the template file 300. For example, lines thirteen through sixteen of the Contact Information table 302 include text that relates to a child of an insurance consumer. The "V7" conditional expression shown in these lines indicates that the text included within the "V7" brackets should be included in the PHA document only if the insurance consumer has a child. Information describing this expression is shown in a first conditional expression area 304 in FIG. 3. Similarly, each of the "CV" labels corresponds to one or more conditions or parameters that indicate that the text included within the corresponding brackets should be selected from a number of options, based on one or more parameters. For example, lines one through eight of the Contact Information table 302 include brackets that include a number of "CV1" labels. The "CV1" conditional expression indicates that the text within the "CV1" brackets should be selected from one of a number of options that include "Employee," "Applicant, "Enrollee," "Associate," and "Cast Member." Information describing this expression is shown in a second conditional expression area 306 in FIG. 3.

FIGS. 4A-4F show an example PHA document 400 that may be generated by the PHA generation module 114 using the method 200 of FIG. 2. The PHA document 400 includes six pages 410, 420, 430, 440, 450, 460, which are shown in FIG. 4A, FIG. 4B, FIG. 4C, FIG. 4D, FIG. 4E, and FIG. 4F, respectively. The PHA document 400 relates to a request for a PHA document on behalf of an example insurance consumer named John Doe and his spouse Jane Doe, who seek insurance coverage via a group insurance plan through John Doe's employer, Associated Products.

As shown in FIG. 4A, page one 410 of the example PHA document 400 includes an Employer Information section 412, an Employee Information section 414, and a Coverage Information section 416. Also as shown in FIG. 4A, information related to John Doe and Associated Products has been pre-filled in the Employer Information section 412, the Employee Information section 414, and the Coverage Information section 416 by the PHA generation module 114 based on information obtained in step 208 and/or step 210 of the method 200 FIG. 2.

Figure 4B:
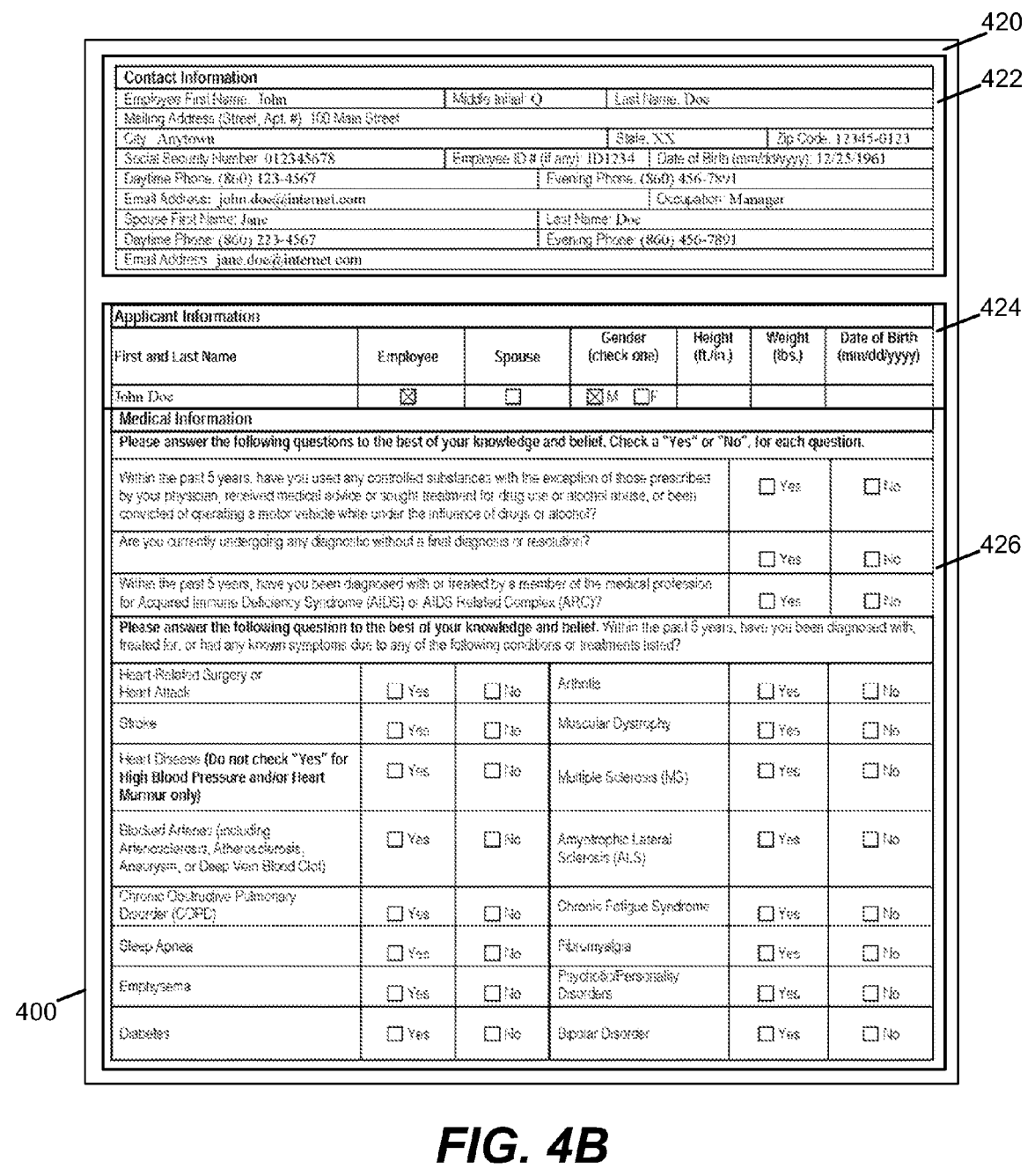

As shown in FIG. 4B, page two 420 of the example PHA document 400 includes a Contact Information section 422, an Applicant Information section 426, and a Medical Information section 426. As shown in FIG. 4B, information related to John Doe has been pre-filled in the Contact Information section 422 and the Applicant Information section 426. The contents of the Contact Information section 422 may be generated by the PHA generation module 114 using, as one example, the portion of the template document 300 described above with reference to FIG. 3.

Figure 4C:
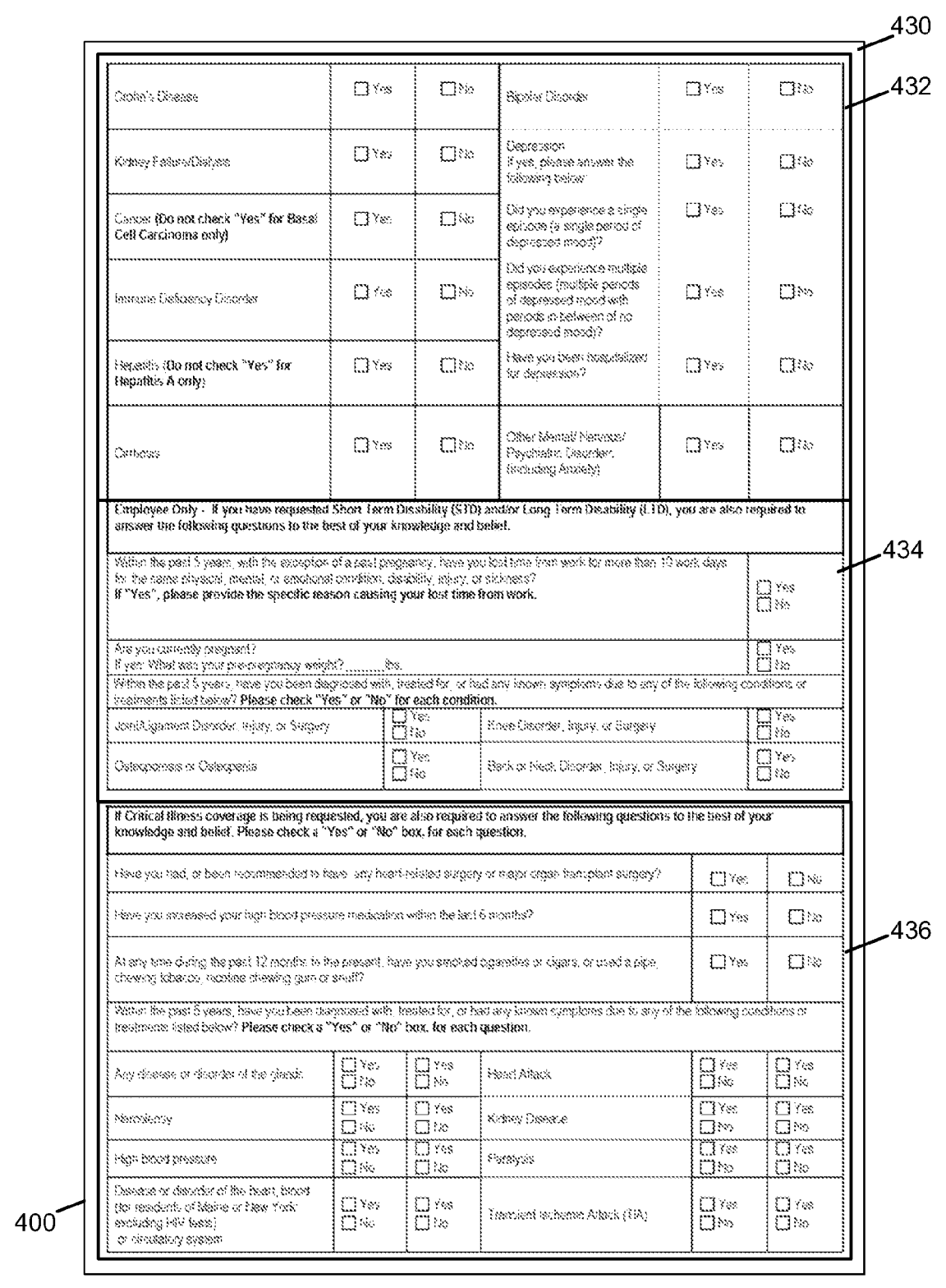

As shown in FIG. 4C, page three 430 of the example PHA document 400 includes an Additional Medical Information section 432 (which is a continuation of the Medical Information section 426 of page two 420), a Disability Coverage section 434, and a Critical Illness Coverage section 436.

As shown in FIG. 4D, page four 440 of the example PHA document 400 includes a Notice section 442, an Authorization section 444, a Fraud section 446, and a Certification section 448.

As shown in FIG. 4E, page five 450 of the example PHA document 400 includes information related to Jane Doe, and includes an Application Information section 452, a Medical Information section 454, and a Critical Illness Coverage section 456.

Figure 4F:
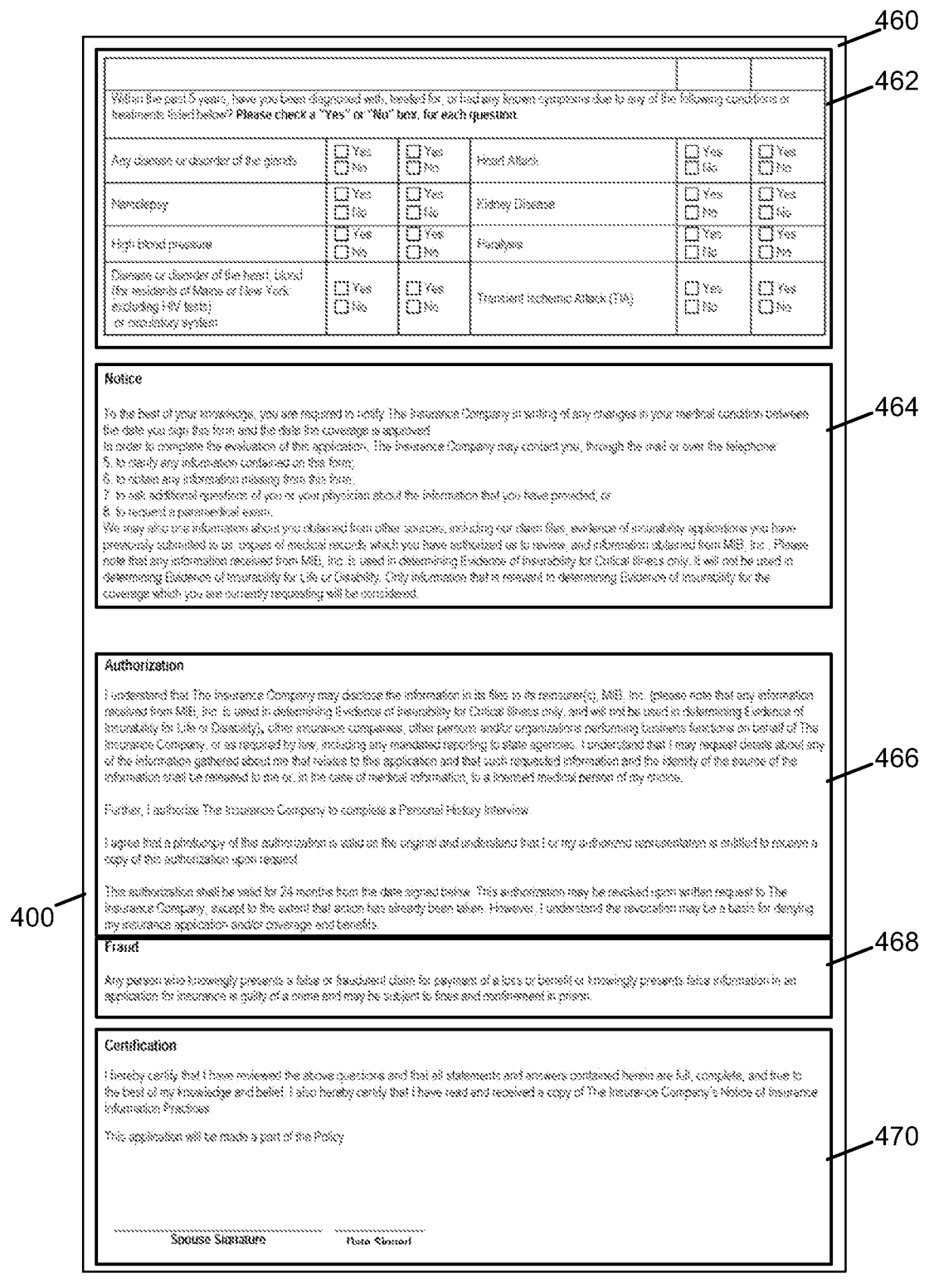

As shown in FIG. 4F, page six 460 of the example PHA document 400 also includes information related to Jane Doe, and includes a second Critical Illness Coverage section 462 (which is a continuation of the Critical Illness Coverage section 456 of page five 450 of the example PHA document 400), a Notice section 464, an Authorization section 466, a Fraud section 468, and a Certification section 470.

Figure 5:
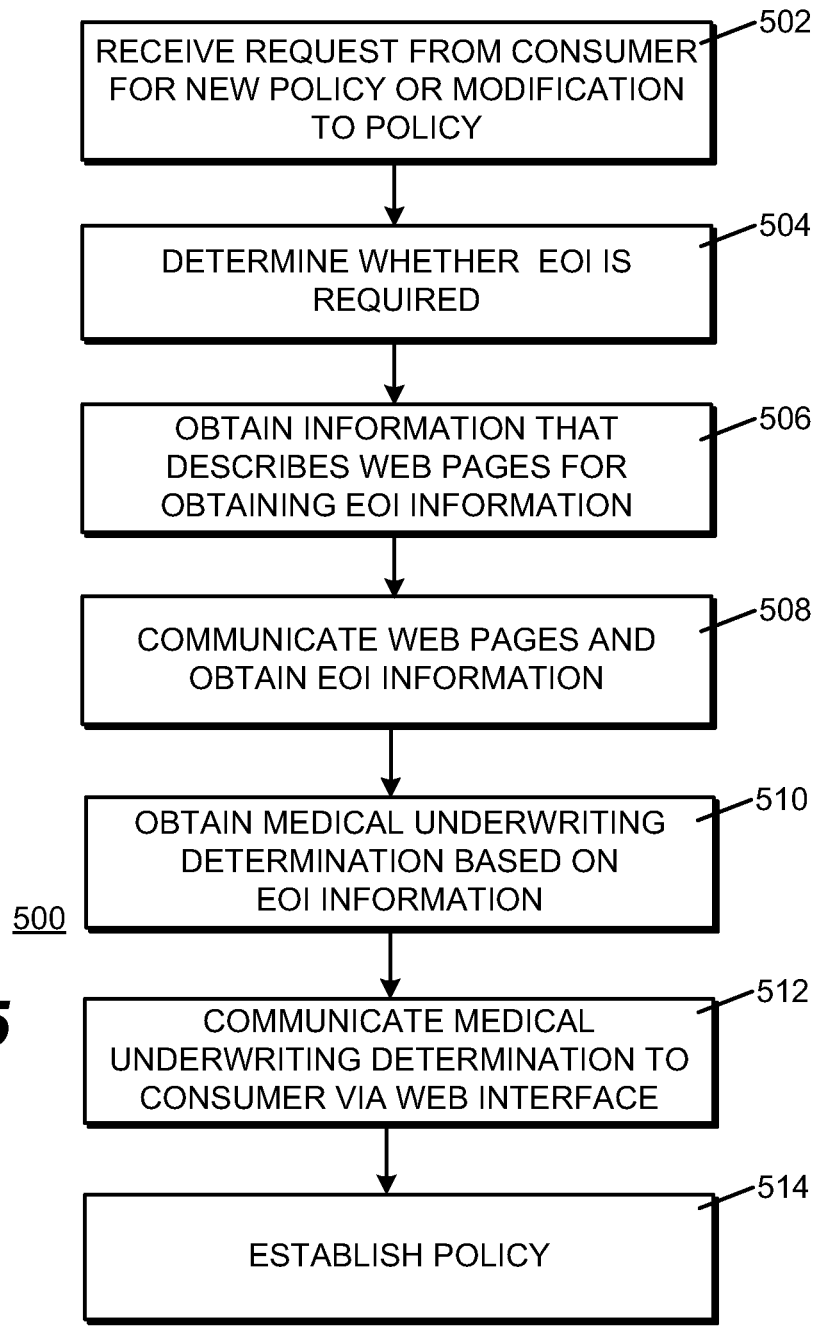
FIG. 5 shows an example method for obtaining an insurance policy or modifying an insurance policy via a web interface.

FIG. 5 shows an example method 500 for obtaining an insurance policy or modifying an insurance policy that may be performed via the web site system 120 of the example architecture 100 of FIG. 1. The method 500 of FIG. 5 begins with the PHA web application module 122 in the web site system 120 receiving information from an insurance consumer via the web browser module 132 that indicates a request for a new policy or a modification to an existing policy (step 502). The request may include an identifier of the insurance consumer, information that describes the policy and/or the modification that the user is requesting, information that indicates the reason for the request (e.g., the insurance consumer is a new hire or has experienced a status change event), and/or other information.

Based on the information in the request, the PHA web application module 122 determines whether EOI is required (step 504). In an instance where EOI is required, the PHA web application module 122 then communicates with the PHA management system 110 to obtain information that describes web pages that may be used to obtain EOI information (step 506). This may include the PHA web application module 122 sending one or more messages to the PHA generation module 114 that indicate that information is required by the PHA web application 112 to solicit EOI information from the insurance consumer. The messages may include, for example, information that describes the policy and/or the modification that the user is requesting, information that indicates the reason for the request, and/or other information. The PHA generation module 114 may then generate the information required by the PHA web application 112, and transmit the information back to the PHA web application 112. As one example of an approach that the PHA generation module 114 may employ to generate the information required by the PHA web application 112, the PHA generation module 114 may perform processing that is similar or analogous to the processing described above with reference to FIG. 2 in step 208, step 210, and step 212. However, instead of generating a PHA document, the PHA generation module 114 may generate information that describes web pages that the PHA web application 112 may use to solicit the same information requested in a PHA document, such as the example PHA document 400 of FIGS. 4A-4F. This information may be defined according to a format such as Web Interface Definition Language (WIDL), Extensible Forms Description Language (XFDL), XForms, a specific-purpose data format, and/or any other appropriate format.

As a variation on step 506, the PHA web application module 112 may not interact with the PHA management system 110 to obtain information that describes the web pages required to obtain EOI information, but may have this information already available. According to this approach, the new PHA web application module 112 may determine the contents of web pages that it transmits to the insurance consumer to obtain EOI information by performing, mutatis mutandis, similar processing as that described above as performed by the PHA generation module 114 in step 208, step 210, and/or step 212 in FIG. 2.

The PHA web application module 122 then communicates with the insurance consumer (via the web browser module 132) to obtain the EOI information (step 508). This may include the PHA web application module 122 transmitting one or more web pages to the web browser module 132. The web pages may be generated based on information received by the PHA web application module in step 506, and/or generated using the variation on step 506 described above. The web pages may include forms and/or data entry fields that solicit EOI information from the insurance consumer. The solicited information may include any combination of the information solicited in the example PHA document 400 of FIGS. 4A-4F, and/or any other appropriate EOI information. The insurance consumer may enter the EOI information into the forms and/or data entry fields, and the web browser module 132 transmitting the EOI information to the PHA web application module 122.

Upon receiving the EOI information, the PHA web application module 122 communicates with the medical underwriting system 160 to obtain a determination as to whether the insurance company will issue the requested policy or modification (step 510). This may include the PHA web application module 122 transmitting the EOI information received in step 508 and/or the information received in the request in step 502 to the medical underwriting system 160. Based on the EOI information transmitted to the medical underwriting system 160, the medical underwriting system 160 may determine that the insurance company approves the policy or modification, denies the policy or modification, or whether their result is still pending (i.e., requires more information in order to determine whether to approve or deny the policy or modification).

The PHA web application module 122 then transmits one or more web pages to the web browser module 132 that indicate the determination made by the medical underwriting system 160 (step 512). The web browser module 132 may then display the one or more web pages to the user of the consumer client device 130. In an instance where the insurance company requires more information in order to determine whether to approve or deny the policy, the web pages may also indicate what additional information is required by the insurance company, and how the insurance consumer may go about providing the additional information to the insurance company.

In an instance where the medical underwriting system 160 has determined that the insurance company will issue the policy or modification, one or more actions are then performed related to the establishment of the policy (step 514). This may include the insurance company issuing the policy, and communicating a certificate of insurance to the insurance consumer that indicates that the new policy or modification has been issued by the insurance company. The insurance company may mail a paper certificate of insurance to the consumer, and/or may transmit an electronic copy of the certificate of insurance to the insurance consumer via the web site system 120, which would be received by the consumer via the web browser module 132. Alternatively or additionally, in an instance where the insurance consumer has obtained a new policy or modification via a group plan via their employer, the one or more actions may include the insurance company notifying the insurance consumer's employer of the new policy or modification. This notification may be performed via paper letter (via mail), or via an electronic communication mechanism such as email. In response to the notification, the employer may begin a payroll deduction from the insurance consumer's wages for paying the premium for the new policy or modification. Also in response to the notification, the employer may establish a period Electronic Funds Transfer (EFT)-based transfer or other type of electronic funds transfer, to periodically transfer the necessary premium amount from a bank account belonging to the employer to a bank account belonging to the insurance company.

Figure 6:
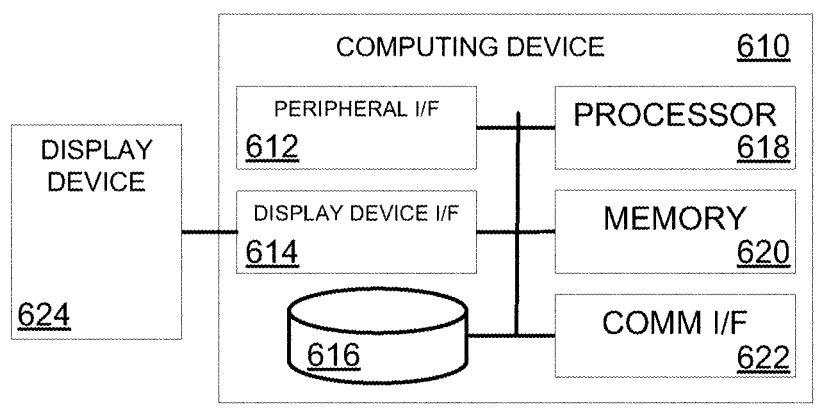
FIG. 6 shows an example computing device that may be used to implement features described herein with reference to FIGS. 1-5.

FIG. 6 shows an example computing device 610 that may be used to implement features describe above with reference to FIGS. 1-5. The computing device 610 includes a processor 618, memory device 620, communication interface 622, peripheral device interface 612, display device interface 614, and storage device 616. FIG. 6 also shows a display device 624, which may be coupled to or included within the computing device 610.

The memory device 620 may be or include a device such as a Dynamic Random Access Memory (D-RAM), Static RAM (S-RAM), or other RAM or a flash memory. The storage device 616 may be or include a hard disk, a magneto-optical medium, an optical medium such as a CD-ROM, a digital versatile disk (DVDs), or Blu-Ray disc (BD), or other type of device for electronic data storage.

The communication interface 622 may be, for example, a communications port, a wired transceiver, a wireless transceiver, and/or a network card. The communication interface 622 may be capable of communicating using technologies such as Ethernet, fiber optics, microwave, xDSL (Digital Subscriber Line), Wireless Local Area Network (WLAN) technology, wireless cellular technology, and/or any other appropriate technology.

The peripheral device interface 612 may be an interface configured to communicate with one or more peripheral devices. The peripheral device interface 612 may operate using a technology such as Universal Serial Bus (USB), PS/2, Bluetooth, infrared, serial port, parallel port, and/or other appropriate technology. The peripheral device interface 612 may, for example, receive input data from an input device such as a keyboard, a mouse, a trackball, a touch screen, a touch pad, a stylus pad, and/or other device. Alternatively or additionally, the peripheral device interface 612 may communicate output data to a printer that is attached to the computing device 610 via the peripheral device interface 612.

The display device interface 614 may be an interface configured to communicate data to display device 624. The display device 624 may be, for example, a monitor or television display, a plasma display, a liquid crystal display (LCD), and/or a display based on a technology such as front or rear projection, light emitting diodes (LEDs), organic light-emitting diodes (OLEDs), or Digital Light Processing (DLP). The display device interface 614 may operate using technology such as Video Graphics Array (VGA), Super VGA (S-VGA), Digital Visual Interface (DVI), High-Definition Multimedia Interface (HDMI), or other appropriate technology. The display device interface 614 may communicate display data from the processor 618 to the display device 624 for display by the display device 624. As shown in FIG. 6, the display device 624 may be external to the computing device 610, and coupled to the computing device 610 via the display device interface 614. Alternatively, the display device 624 may be included in the computing device 600.

An instance of the computing device 610 of FIG. 6 may be configured to perform any feature or any combination of features described above as performed by the consumer client device 130. In such an instance, the memory device 620 and/or the storage device 616 may store instructions which, when executed by the processor 618, cause the processor 618 to perform any feature or any combination of features described above as performed by the web browser module 132. Alternatively or additionally, in such an instance, each or any of the features described above as performed by the web browser module 132 may be performed by the processor 618 in conjunction with the memory device 620, communication interface 622, peripheral device interface 612, display device interface 614, and/or storage device 616.

Figure 7:
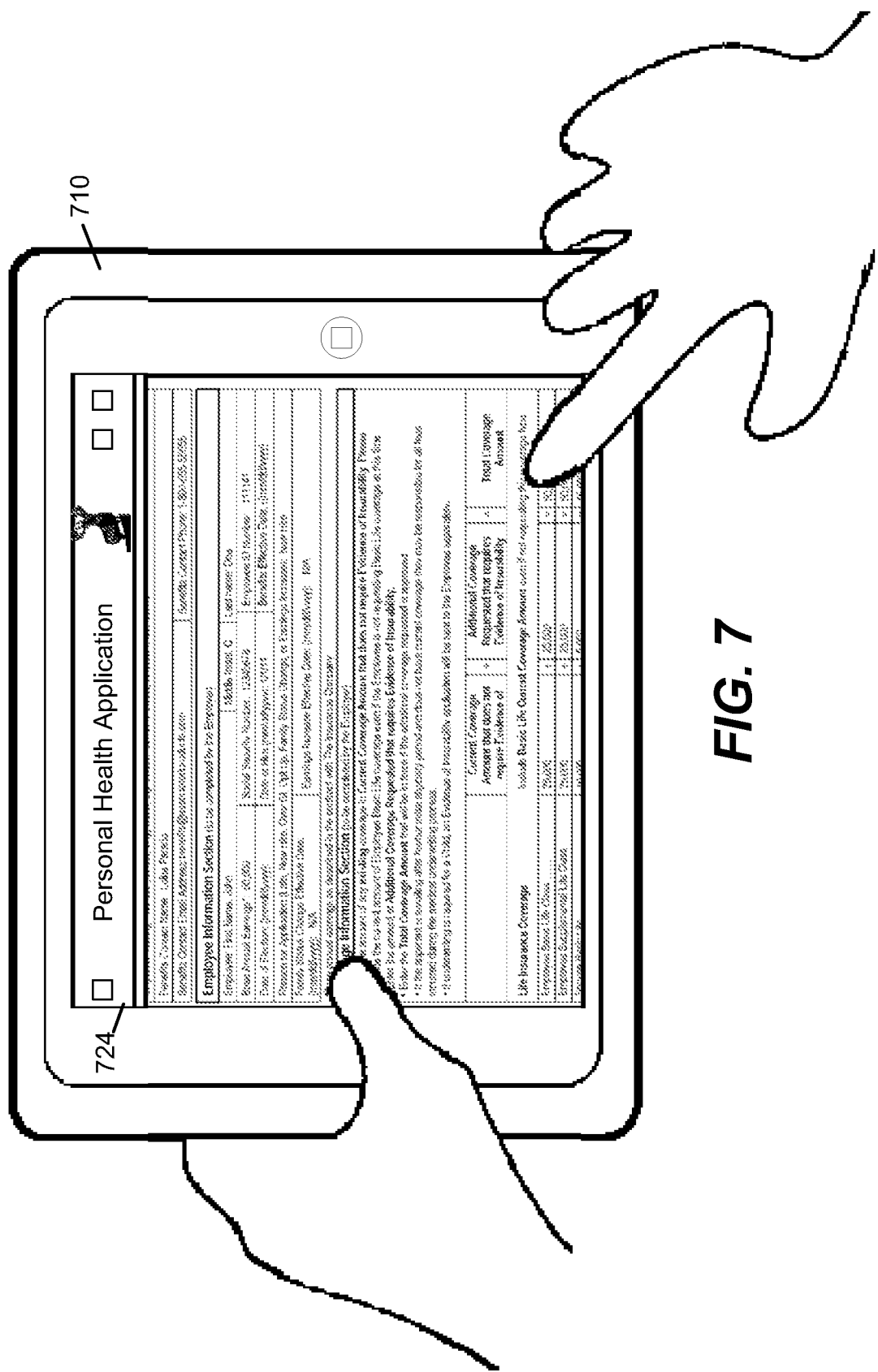
FIG. 7 is a tablet computer that is a more specific example of the computing device of FIG. 6.

FIG. 7 shows a tablet computer 710 that is a more specific example of the computing device 610 of FIG. 6. The tablet computer 710 may include a processor (not depicted), memory device (not depicted), communication interface (not depicted), peripheral device interface (not depicted), display device interface (not depicted), storage device (not depicted), and touch screen display 724, which may possess characteristics of the processor 618, memory device 620, communication interface 622, peripheral device interface 612, display device interface 614, storage device 616, and display device 624, respectively, as described above with reference to FIG. 6. The touch screen display 724 may receive user input using technology such as, for example, resistive sensing technology, capacitive sensing technology, optical sensing technology, or any other appropriate touch-sensing technology. As shown in FIG. 7, the touch screen display 724 may display an electronic PHA document, with characteristics of any or any combination of PHA documents described above with reference to FIGS. 1-6. The touch screen display 724 may receive input from a user of the tablet computer 710, for filling in the PHA document shown in the touch screen display 724.

Referring again to FIG. 6, an instance of the computing device 610 may alternatively or additionally be configured to perform any feature or any combination of features described above as performed by the PHA management system 110. In such an instance, the memory device 620 and/or the storage device 616 may store instructions which, when executed by the processor 618, cause the processor 618 to perform any feature or any combination of features described above as performed by the interface module 112 and/or the PHA generation module 114. In such an instance, the processor 618 may perform the feature or combination of features in conjunction with the memory device 620, communication interface 622, peripheral device interface 612, display device interface 614, and/or storage device 616.

Alternatively or additionally, an instance of the computing device 610 may be configured to perform any feature or any combination of features described above as performed by the administrative client device 140. In such an instance, the memory device 620 and/or the storage device 616 may store instructions which, when executed by the processor 618, cause the processor 618 to perform any feature or any combination of features described above as performed by the administrative client module 142. In such an instance, the processor 618 may perform the feature or combination of features in conjunction with the memory device 620, communication interface 622, peripheral device interface 612, display device interface 614, and/or storage device 616.

Alternatively or additionally, an instance of the computing device 610 may be configured to perform any feature or any combination of features described above as performed by the PHA client device 150. In such an instance, the memory device 620 and/or the storage device 616 may store instructions which, when executed by the processor 618, cause the processor 618 to perform any feature or any combination of features described above as performed by the PHA client module 152. In such an instance, the processor 618 may perform the feature or combination of features in conjunction with the memory device 620, communication interface 622, peripheral device interface 612, display device interface 614, and/or storage device 616.

Alternatively or additionally, an instance of the computing device 610 may be configured to perform any feature or any combination of features described above as performed by the web site system 120. In such an instance, the memory device 620 and/or the storage device 616 may store instructions which, when executed by the processor 618, cause the processor 618 to perform any feature or any combination of features described above as performed by the PHA web application module 122 and/or the HTTP server module 124. In such an instance, the processor 618 may perform the feature or combination of features in conjunction with the memory device 620, communication interface 622, peripheral device interface 612, display device interface 614, and/or storage device 616.

Although FIG. 6 shows that the computing device 610 includes a single processor 618, single memory device 620, single communication interface 622, single peripheral device interface 612, single display device interface 614, and single storage device 616, the computing device may include multiples of each or any combination of these components 618, 620, 622, 612, 614, 616, and may be configured to perform, mutatis mutandis, analogous functionality to that described above.

As used herein, the term "processor" broadly refers to and is not limited to a single- or multi-core processor, a special purpose processor, a conventional processor, a Graphics Processing Unit (GPU), a digital signal processor (DSP), a plurality of microprocessors, one or more microprocessors in association with a DSP core, a controller, a microcontroller, one or more Application Specific Integrated Circuits (ASICs), one or more Field Programmable Gate Array (FPGA) circuits, any other type of integrated circuit (IC), a system-on-a-chip (SOC), and/or a state machine.

As used to herein, the term "computer-readable medium" broadly refers to and is not limited to a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVDs, or BD, or other type of device for electronic data storage.

Although the methods and features described above with reference to FIGS. 1-7 are described above as performed using the example architecture 100 of FIG. 1, the methods and features described above may be performed, mutatis mutandis, using any appropriate architecture and/or computing environment. Although features and elements are described above in particular combinations, each feature or element can be used alone or in any combination with or without the other features and elements. For example, each feature or element as described above with reference to FIGS. 1-7 may be used alone without the other features and elements or in various combinations with or without other features and elements. Sub-elements of the methods and features described above with reference to FIGS. 1-7 may be performed in any arbitrary order (including concurrently), in any combination or sub-combination.

What is claimed is:

1. A system for generating a customized Personal Health Application document related to an insurance policy associated with a group insurance plan, the system comprising:
   a communication interface configured to receive a message from a computing device that indicates a request for a customized Personal Health Application document for obtaining evidence of insurability information and identifying the insurance consumer, wherein the group insurance plan is offered by an employer of the insurance consumer; and
   at least one processor configured to:
      obtain consumer data that indicates one or more attributes of the insurance consumer;
      obtain employer data that indicates one or more attributes of the employer of the insurance consumer;
      obtain jurisdiction data that identifies a jurisdiction whose legal requirements apply to the customized Personal Health Application document; and
      obtain a template document including data and at least a first conditional expression and a second conditional expression, the template document for generating the customized Personal Health Application document, including information that indicates a plurality of questions that solicit evidence of insurability information;
      evaluate the first conditional expression to filter a first question from the plurality of questions to indicate whether the first question from the plurality of questions should be included in the customized Personal Health Application document based on at least one of the consumer data, the employer data, and the jurisdiction data;
      evaluate the second conditional expression to indicate that concepts identified in the template document be described using particular words or phrases in the customized Personal Health Application document as determined based on at least one of the consumer data, the employer data, and the jurisdiction data; and
   generate the customized Personal Health Application document including the first filtered question and the described concepts, wherein the document is based on the template data, the insurance consumer data, the employer data, and the jurisdiction data; and
   wherein the communication interface is further configured to transmit the customized Personal Health Application document to the computing device for presentation to the insurance consumer,
      wherein the plurality of questions includes a second question, wherein the second question solicits information that the insurance consumer is required to provide to in order to obtain a disability insurance policy, and
      wherein the template data includes a third conditional expression that indicates that the second question should be included in the customized Personal Health Application document when the insurance policy within a group insurance plan is a disability insurance policy.

2. The system of claim 1, wherein the first question solicits information related to a Human Immunodeficiency Virus status of the insurance consumer, and wherein the first conditional expression indicates whether the first question should be included in the Personal Health Application document based on the jurisdiction data.

3. The system of claim 1, wherein the section of the Personal Health Application document is a fraud warning section, and wherein the second conditional expression indicates that the contents of the section of the Personal Health Application document should be determined based on the jurisdiction data.

4. The system of claim 1,
   wherein the first question solicits information regarding a spouse of the insurance consumer, and
   wherein the first conditional expression indicates that, if the insurance consumer has a spouse, the first question should be included in the Personal Health Application document.

5. The system of claim 1, wherein the at least one processor is further configured to pre-fill information related to the insurance consumer in the Personal Health Application document, wherein the information related to the insurance consumer includes one or more of: a name of the consumer; an address of the consumer; a gender of the consumer; a phone number of the consumer; and a name of an occupation of the consumer.

6. The system of claim 1, wherein the request by the insurance consumer for the insurance policy is a request for a supplemental life insurance policy.

7. A computer-implemented method for generating a customized Personal Health Application document for obtaining evidence of insurability information and identifying the insurance consumer, the method comprising:
   receiving, via a communication interface, a message from a computing device that indicates a request for a customized Personal Health Application document related to an insurance policy;
   at least one processor obtaining a template document including data and at least a first conditional expression, the template document for generating the customized Personal Health Application document, the template data including information that indicates a plurality of questions that solicit evidence of insurability information;
   the at least one processor calculating the first conditional expression to filter a first question from the plurality of questions to indicate whether the first question from the plurality of questions should be included in the customized Personal Health Application document based on at least one of consumer data that indicates one or more attributes of the insurance consumer, and jurisdiction data that identifies a jurisdiction whose legal requirements apply to the customized Personal Health Application document;
   the at least one processor generating the customized Personal Health Application document including the first filtered question, wherein the document is based on the template data, and the calculation of the first conditional expression; and transmitting, via the communication interface, the customized Personal Health Application document to the computing device for presentation to the insurance consumer, wherein the template data includes a second conditional expression that indicates that contents of a section of the customized Personal Health Application document should be determined based on one or more of: the insurance consumer data; the employer data; or the jurisdiction data, and wherein the generating the customized Personal Health Application document includes evaluating the second conditional expression.

8. The method of claim 7, wherein the first question solicits information related to a Human Immunodeficiency Virus status of the insurance consumer, and wherein the first conditional expression indicates whether the first question should be included in the Personal Health Application document based on the jurisdiction data.

9. The method of claim 7, wherein the insurance policy is an insurance policy within a group insurance plan offered by an employer of the insurance consumer.

10. The method of claim 9, wherein the first conditional expression further indicates whether the first question from the plurality of questions should be included in the Personal Health Application document based on employer data that that indicates one or more attributes of the employer of the insurance consumer.

11. The method of claim 7, wherein the section of the Personal Health Application document is a fraud warning section, and wherein the second conditional expression indicates that the contents of the section of the Personal Health Application document should be determined based on the jurisdiction data.

12. The method of claim 7,
wherein the insurance consumer data indicates whether the insurance consumer has a spouse,
wherein the plurality of questions includes a second question, wherein the second question solicits information regarding a spouse of the insurance consumer,
wherein the template data includes a second conditional expression that indicates that, if the insurance consumer has a spouse, the second question should be included in the Personal Health Application document, and
wherein the generating the Personal Health Application document includes evaluating the second conditional expression.

13. The method of claim 7,
wherein the plurality of questions includes a second question, wherein the second question solicits information that the insurance consumer is required to provide to in order to obtain a disability insurance policy, and
wherein the template data includes a second conditional expression that indicates that the second question should be included in the Personal Health Application document when the insurance policy to which the Personal Health Application document is related is a disability insurance policy.

14. A non-transitory computer-readable medium having processor-executable instructions stored thereon which, when executed by at least one processor, will cause the at least one processor to perform a method for generating a customized Personal Health Application document, the method comprising:

receiving, via a communication interface, a message from a computing device that indicates a request for a customized Personal Health Application document related to an insurance policy;

obtaining a template document including data and one or more conditional expressions, the template documents for generating the customized Personal Health Application document, wherein the template document includes:
information that indicates a plurality of questions that solicit evidence of insurability information; and
one or more conditional expressions for determining content to include in the customized Personal Health Application document;

generating the customized Personal Health Application document based on the template data, wherein the generating the customized Personal Health Application document includes evaluating the one or more conditional expressions; and transmitting, via the communication interface, the customized Personal Health Application document to the computing device, wherein the one or more conditional expressions include a first conditional expression that indicates whether a first question from the plurality of questions should be included in the customized Personal Health Application document based on one or more of:
insurance consumer data that indicates one or more attributes of the insurance consumer;
employer data that that indicates one or more attributes of an employer of the insurance consumer; or
jurisdiction data that identifies a jurisdiction whose legal requirements apply to the customized Personal Health Application document.

15. The non-transitory computer-readable medium of claim 14, wherein the first question solicits information related to a Human Immunodeficiency Virus status of the insurance consumer, and wherein the first conditional expression indicates whether the first question should be included in the Personal Health Application document based on the jurisdiction data.

16. The non-transitory computer-readable medium of claim 14, wherein the insurance policy is associated with a group insurance plan offered by an employer of the insurance consumer.

17. The non-transitory computer-readable medium of claim 14,
wherein the one or more conditional expressions include a first conditional expression that indicates that contents of a section of the Personal Health Application document should be determined based on one or more of:
insurance consumer data that indicates one or more attributes of the insurance consumer;
employer data that that indicates one or more attributes of an employer of the insurance consumer; or
jurisdiction data that identifies a jurisdiction whose legal requirements apply to the Personal Health Application document.

18. The non-transitory computer-readable medium of claim 17, wherein the section of the customized Personal Health Application document is a fraud warning section, and wherein the first conditional expression indicates that the contents of the section of the customized Personal Health Application document should be determined based on the jurisdiction data.

19. The non-transitory computer-readable medium of claim 14, wherein the plurality of questions includes a first question, wherein the first question solicits information regarding a spouse of the insurance consumer, and wherein the one or more conditional expressions include a conditional expression that indicates that, if the insurance consumer has a spouse, the first question should be included in the customized Personal Health Application document.

20. The non-transitory computer-readable medium of claim 14, wherein the plurality of questions includes a first question, wherein the first question solicits information that the insurance consumer is required to provide to in order to obtain a disability insurance policy, and wherein the one or more conditional expressions include a conditional expression that indicates that the first question should be included in the customized Personal Health Application document when the insurance policy to which the customized Personal Health Application document is related is a disability insurance policy.

* * * * *

UNITED STATES PATENT AND TRADEMARK OFFICE
CERTIFICATE OF CORRECTION

| | | |
|---|---|---|
| PATENT NO. | : 8,805,706 B2 | Page 1 of 1 |
| APPLICATION NO. | : 13/097560 | |
| DATED | : August 12, 2014 | |
| INVENTOR(S) | : Cunningham et al. | |

It is certified that error appears in the above-identified patent and that said Letters Patent is hereby corrected as shown below:

IN THE SPECIFICATION

At column 5, line 53, after the words "in the", delete the second occurrence of the words "in the";
At column 6, line 62, after the words "using one or", insert therefor --more--;
At column 7, line 46, delete "an" and insert therefor --and--;
At column 7, line 59, delete "operated" and insert therefor --operator--;
At column 7, line 67, after "determines", delete "whether";
At column 17, line 2, change "DVDs" to "DVD";

IN THE CLAIMS

In claim 1, at column 18, line 3, after the words "to provide", delete "to";
In claim 10, at column 19, line 30, delete "that";
In claim 13, at column 19, line 54, after the words "to provide", delete "to";
In claim 14, at column 20, line 30, after the words "data that", delete "that";
In claim 17, at column 20, line 54, after the words "data that", delete "that";
In claim 20, at column 21, line 13, after the words "to provide", delete "to".

Signed and Sealed this
Seventh Day of July, 2015

Michelle K. Lee
*Director of the United States Patent and Trademark Office*